United States Patent [19]

Smith-Lewis et al.

[11] 4,166,093

[45] Aug. 28, 1979

[54] REDUCTION OF DETECTABLE SPECIES MIGRATION IN ELEMENTS FOR THE ANALYSIS OF LIQUIDS

[75] Inventors: Margaret J. Smith-Lewis, Pittsford; John Figueras, Victor, both of N.Y.

[73] Assignee: Eastman Kodak Company, Rochester, N.Y.

[21] Appl. No.: 916,173

[22] Filed: Jun. 16, 1978

Related U.S. Application Data

[63] Continuation-in-part of Ser. No. 822,987, Aug. 8, 1977, abandoned.

[51] Int. Cl.$^2$ .................... G01N 21/06; G01N 31/22; G01N 33/16
[52] U.S. Cl. ........................................ 422/56; 435/14; 422/57
[58] Field of Search .................... 422/56; 23/230 B; 195/103.5 R, 103.5 C

[56] References Cited

U.S. PATENT DOCUMENTS

| | | | |
|---|---|---|---|
| 3,585,112 | 6/1971 | Ernst | 195/103.5 R |
| 3,901,657 | 8/1975 | Lightfoot | 422/56 |
| 3,917,453 | 11/1975 | Milligan et al. | 422/56 X |
| 3,992,158 | 11/1976 | Przybylowicz et al. | 422/57 |
| 3,993,451 | 11/1976 | Verbeck | 422/57 |
| 4,042,335 | 8/1977 | Clement | 422/56 |
| 4,050,898 | 9/1977 | Goffe et al. | 422/57 |
| 4,066,403 | 1/1978 | Bruschi | 422/57 X |

Primary Examiner—Arnold Turk
Attorney, Agent, or Firm—Ronald P. Hilst

[57] ABSTRACT

An element for the analysis of liquids contains a radiation-transmissive, detectable species migration-inhibiting layer interposed between a porous radiation-blocking layer and a radiation-transmissive reagent layer. All three layers are permeable to a predetermined analyte. The reagent layer contains a composition that provides a detectable species such as a dye in proportion to the concentration of the analyte that diffuses into the reagent layer from the overlying porous radiation-blocking layer. The detectable species migration-inhibiting layer acts to reduce the migration of, for example, dye from the reagent layer into the porous radiation-blocking layer, where the optical density of the dye cannot easily be measured. Optionally, the above-described three layers can be carried on a radiation-transmissive support, and other layers such as spreading layers, registration layers, and subbing layers can also be present in the element.

17 Claims, 2 Drawing Figures

18 OPTIONAL SPREADING LAYER
16 POROUS RADIATION-BLOCKING LAYER
14 DETECTABLE SPECIES MIGRATION-INHIBITING LAYER
12 REAGENT LAYER

REDUCTION OF DETECTABLE SPECIES MIGRATION IN ELEMENTS FOR THE ANALYSIS OF LIQUIDS

This is a continuation-in-part application of U.S. Ser. No. 822,987, filed Aug. 8, 1977, and now abandoned.

BACKGROUND OF THE INVENTION

1. Field of the Invention

The present invention relates to an improved element for the chemical analysis of liquids. More particularly it concerns multilayer elements that provide a means for determining the presence and/or concentration of a substance in a liquid by effecting the release or formation of a detectable species, such as a dye, within the element in quantities proportionate to the concentration of the substance in the liquid being analyzed. The present invention provides a means for inhibiting the migration or wandering of a substantial portion of this detectable species to areas or layers of the element in which the presence of the detectable species cannot easily be determined, either quantitatively or qualitatively.

2. Description of Related Art

It is often desirable or necessary to determine the presence and/or concentration of certain substances in liquids such as water, foodstuffs, and biological liquids. A variety of devices and methods have been employed for such analyses.

Various inexpensive elements have been devised to facilitate rapid and convenient analyses under other than controlled laboratory conditions. Such elements often include a reagent for the analyte (the term analyte referring to the substance being analyzed for in the liquid sample). This reagent, upon contact with the analyte, causes the formation of a dye or brings about some other detectable change to indicate the presence of analyte in the liquid sample. One example of such an element is a pH test strip that comprises a paper or other absorbent material impregnated with an appropriate reagent or reagents. Simple elements of this type are most often employed when it is only necessary to make a quick visual determination of the presence of the analyte qualitatively or at best semi-quantitatively.

More sophisticated elements are available for quantitative diagnostic analyses of biological liquids like blood or urine. When a liquid sample containing the analyte is brought into contact with these elements, they form the dye or other detectable change consistently and uniformly within the element in proportion to the concentration of the analyte in the liquid sample. Analyte concentration can then be determined, for example, by spectrophotometric measurement of the optical density of the dye formed in the element.

Elements of this type are described in U.S. Pat. No. 3,992,158, issued Nov. 16, 1976. These elements can consist of two or more desirably discrete layers that are superposed and in substantially continuous intimate contact with adjacent layers. One such multilayer element comprises a support layer having a reagent layer and an outermost spreading layer coated upon it. In this multilayer element, the spreading layer serves as a liquid sample permeable receiving and metering layer. That is, the liquid sample to be analyzed is placed on the spreading layer, which absorbs and transfers the liquid into the reagent layer. Preferably, as described in U.S. Pat. No. 3,992,158, the spreading layer is isotropically porous and transfers a uniform concentration (as measured across a per unit cross-sectional area of the spreading layer) of the analyte contained in the liquid sample to the underlying reagent layer. The reagent layer has certain reagents uniformly distributed therein. A detectable species such as a dye is formed within the reagent layer in an amount proportional to the concentration of analyte in the liquid. Typically, the reagent and support layers are radiation-transmissive so that a spectrophotometric measurement of the optical density of the dye formed in the reagent layer can be made with the element remaining intact. Additionally, the spreading layer may comprise a blushed polymer and a pigment to provide both uniform transfer of the liquid sample to the reagent layer and an opaque, reflective surface above the reagent layer to aid in a measurement of reflection density of the dye. With this element, however, some of the dye formed in the reagent layer may migrate or wander into the opaque spreading layer where it would not be detected during the dye-density measurement, thereby reducing the sensitivity and the accuracy of the analysis.

Related elements are described in U.S. Pat. No. 4,042,335, of Clement, issued Aug. 16, 1977. A registration layer and an opaque or radiation-blocking layer are coated between the support layer and the reagent layer. During the analysis, a significant portion of the detectable species, e.g., a dye, formed in the reagent layer will diffuse through the radiation-blocking layer and into the registration layer, where the dye density will be measured. A mordant for the dye can be included in the registration layer to insure that the dye that has diffused into this layer will be fixed there for easy detection and will not be allowed to diffuse or migrate out of the registration layer. Elements such as this are suggested for use where it would not otherwise be practical to reliably measure the dye density within the reagent layer itself, for example, in analytical elements where other reagents and reaction products within the reagent layer also provide density, thus preventing any accurate spectrophotometric measurement of the optical density in this layer of only the dye. Such an element can provide a reliable analysis. However, it is obvious that a significant portion of the dye formed during the analysis can remain in the reagent layer or migrate into and remain in the radiation-blocking layer. The sensitivity and accuracy of the analytical element are thereby reduced, because the analyte-concentration determination must depend upon the measurement of the density of a smaller amount of dye than that which was actually formed.

Other elements as described in U.S. Pat. No. 3,585,112 and U.S. Pat. No. 3,917,453 disclose means for overcoming these problems. Both of these patents suggest the use of mordants in the reaction zone or layer to provide a degree of immobility to the indicator dye formed. These elements, like others of the prior art, however, are susceptible to the additional problem of the mordant interfering with the formation of the dye or interfering with any prerequisite reactions leading to the formation of the dye. Such interference can make the analysis completely unreliable.

Accordingly, it is desirable to provide an analytical element that has all of the advantages of the elements described above, i.e., ease of use, low cost and quantitative results; and that also overcomes the problems inherent in prior art elements, such as reduced sensitivity and accuracy of results caused by (a) migration of detectable species into porous radiation-blocking layers and (b) interference with the formation or release of the detectable species by mordants used to inhibit such migrations.

SUMMARY OF THE INVENTION

The elements of the present invention have unexpectedly overcome the problems of prior art analytical elements, namely by providing for quantitative analyses which are highly accurate and sensitive. The present elements do so by inhibiting migration of the detectable species from the reagent layer to layers of the element where such species could not easily be measured, and by providing a means for avoiding interference with the reaction or reactions that result in detectable species formation in or release from the reagent layer. Elements according to this invention can be used for diagnostic purposes and include: a radiation-transmissive reagent layer, permeable to, and containing a composition interactive with, a predetermined analyte (or reaction product thereof) to provide a radiometrically detectable species; a porous radiation-blocking layer permeable to the analyte; and the improvement of having a radiation-transmissive, detectable species migration-inhibiting layer, permeable to the analyte and interposed between the reagent layer and the radiation-blocking layer. This layer prevents a substantial amount of the detectable species which may diffuse out of the reagent layer from entering the porous radiation-blocking layer where it is not practically measurable, by fixing such migrating detectable species within the detectable species migration-inhibiting layer, where it is easily detectable. Another advantage of the present invention is that the detectable species migration-inhibiting layer is separate from the reagent layer, so that it does not interfere with the analytical interaction(s) taking place in the reagent layer.

Optionally, analytical elements of the present invention can be carried on a radiation-transmissive support, and other layers such as spreading layers, registration layers, and subbing layers can also be present in the element. Also, the porous radiation-blocking layer can itself function as a spreading layer in some embodiments of the present invention.

BRIEF DESCRIPTION OF THE DRAWINGS

In the accompanying drawings each of FIG. 1

DESCRIPTION OF THE PREFERRED EMBODIMENTS

Figure 1:
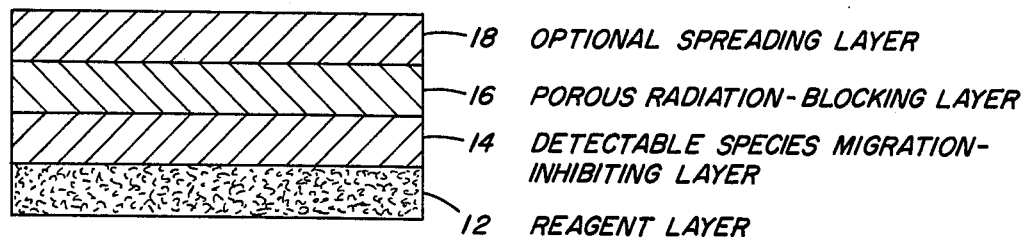

The analytical elements of this invention are multilayered, consisting of three or more desirably discrete layers that are superposed and in fluid contact with each other under conditions of use. These layers include a reagent layer, a porous radiation-blocking layer, and a detectable species migration-inhibiting layer. In certain embodiments of the invention the porous radiation-blocking layer can function also as a spreading layer, or there can be a separate spreading layer in addition to the porous radiation-blocking layer. In other embodiments the element can include a radiation-transmissive support layer in addition to the three layers described above. In still other embodiments additional radiation-transmissive layers, e.g., subbing layers or registration layers, can also be included in the analytical element.

In the present invention the layers are always arranged such that the detectable species migration-inhibiting layer is interposed between the porous radiation-blocking layer and the reagent layer. In those embodiments containing an additional layer to function as a spreading layer, the porous radiation-blocking layer is interposed between the spreading layer and the detectable species migration-inhibiting layer. In those embodiments containing a radiation-transmissive support layer, the reagent layer is interposed between the detectable species migration-inhibiting layer and the radiation-transmissive support layer. In those embodiments containing additional radiation-transmissive layers, such as subbing or registration layers, the additional subbing layers or registration layers are interposed between the reagent layer and the optional radiation-transmissive support layer.

U.S. Pat. No. 3,992,158 and Clement, U.S. Pat. No. 4,042,335 issued Aug. 16, 1977, both incorporated herein by reference, disclose reagent layers, porous radiation-blocking layers, support layers, subbing layers, registration layers, and preferred types of isotropically porous spreading layers, that are useful in the practice of the present invention. These materials also describe well known methods of preparing these layers to form individual multilayer elements and describe the use of such elements for various quantitative analyses.

As used herein, the term, porous radiation-blocking layer, defines a layer that is permeable to a predetermined analyte (or reaction product thereof) dissolved or dispersed in a liquid, and that reflects, or optionally absorbs, detecting radiation, i.e., radiation used together with the elements of the invention to facilitate result detection of the particular detectable species which is provided by the reagent layer. In other words, the porous radiation-blocking layer will allow the predetermined analyte to pass through it, and it is used together with suitable detecting radiation to facilitate result detection in the analytical elements of the invention such as by reflection photometry. Because of the radiation-blocking properties of the porous radiation-blocking layer, the radiative properties, i.e., the particular emissive, transmissive, or absorptive properties, of any of the detectable species which migrates into this layer can be substantially masked or hidden. Therefore, detecting radiation used to determine the presence or absence of detectable species formed in the reagent layer may be unable to accurately detect that portion of the detectable species which, although provided in response to a given analyte, has migrated into the porous radiation-blocking layer.

As noted above, the analytical elements of the present invention can optionally contain a separate spreading layer in addition to the porous radiation-blocking layer, or the porous radiation-blocking layer itself can also function as a spreading layer. Like the porous radiation-blocking layer, a spreading layer must be permeable to a predetermined analyte dissolved or dispersed in a liquid. When liquid containing the analyte is brought into contact with the outermost surface of a spreading layer, the spreading layer distributes the liquid within itself such that the concentration of the analyte provided at the surface of the spreading layer that faces the reagent layer of the element is regulated or controlled. Preferably, but not necessarily, the spreading layer is isotropically porous and delivers a uniform concentration of analyte to the reagent layer. In one embodiment of the present invention a separate spreading layer may be included in addition to the porous radiation-blocking layer, as noted above, and in such case the spreading layer may be either radiation-transmissive or radiation-blocking. Radiation-transmissive, as used herein, defines the ability to transmit detecting radiation used to determine the presence, optionally the absence, of the detectable species provided by the reagent layer. If desired, one or more interactive or reagent compositions may be incorporated in the spreading layer or separate porous radiation-blocking layer to interact with the analyte of choice, thereby forming an analyte reaction product which can undergo further interaction in the underlying reagent layer as described hereinafter.

In one preferred embodiment of the present invention the porous radiation-blocking layer itself functions as an adequate spreading layer and comprises a blushed polymer and optionally a finely-divided particulate material such as a pigment. Layers of this type are discussed in detail in U.S. Pat. No. 3,992,158 and U.S. Pat. No. 4,042,335. Useful blushed polymers include cellulose acetate, amides, and the like. Useful particulate materials include pigments such as carbon, titanium dioxide, barium sulfate, and the like.

Reagent layers in the elements of this invention are radiation-transmissive, that is, they will transmit light in the range of the spectrum used to determine the presence and/or concentration of the detectable species provided by the reagent layer. Preferably, the reagent layer is uniformly permeable to the particular analyte to be measured. Within the reagent layer is distributed a material that can interact with the analyte or reaction product of the analyte. Such interaction causes the release of a preformed detectable species or the formation of such a detectable species within the reagent layer, preferably, in proportion to the concentration of the analyte in the liquid sample being analyzed. Such interaction is meant to refer to chemical activity, catalytic activity as in the formation of an enzyme-substrate complex, and any other form of chemical or physical interaction that can release, produce, or otherwise provide within the reagent layer a species that is radiometrically detectable, that is, by suitable measurement of light or other energy. Typically, the detectable species formed or released from the reagent layer is a dye which is radiometrically detectable by fluorometric or colorimetric, preferably colorimetric techniques.

In addition, if necessary or desirable, appropriate buffer compositions may also be present in the reagent layer. Reagent layers of the present invention may also contain one or more hydrophilic colloids including natural colloids such as gelatin, agarose, polysaccharides, and the like; and/or synthetic resins such as poly(vinyl alcohol), poly(vinyl pyrrolidone), polyacrylamides, and the like.

One application of the present invention comprises an element for the analysis of glucose in liquids wherein the interactive material in the reagent layer preferably comprises glucose oxidase, peroxidase, and an indicator composition. A useful indicator composition comprises 4-aminoantipyrene hydrochloride and 7-hydroxy-1-naphthol. In the presence of glucose, the above interactive material effects the formation of a dye in proportion to the concentration of glucose in the sample being analyzed. This concentration can then be determined by spectrophotometrically measuring the optical density of the dye formed and performing an arithmetic calculation. Another embodiment of the present invention comprises an element for the analysis of calcium in liquids and includes a reagent layer containing an interactive material which is an indicator for calcium and forms a colored species in the presence of calcium, such as chlorophosphonazo III or arsenazo III. The use of arsenazo III as a calcium complexing agent is described in *Anal. Chim. Acta.*, Vol. 53 (1971), p. 194–198. Other suitable indicators for calcium are known and may be found, for example, in *Clinical Chemistry Principles and Technics*, edited by Henry et. al., 2nd. ed., chapter 19, p. 648, published by Harper and Row (1974). Elements of the present invention are also useful in the analysis of many other substances in liquids in addition to calcium or glucose as noted above.

As stated hereinabove, the elements of this invention can also include a radiation-transmissive support to support the other layers. Such a support transmits light in the range of the spectrum used to determine the presence and/or absence of detectable species provided by the reagent layer. In the case where the detectable species is a visibly colored material, e.g., a dye, this will allow the spectrophotometric measurement of the dye density to be performed through the support layer with all layers of the element still intact. A useful support layer can comprise cellulose acetate, polyethylene terephthalate, and the like.

Other optional layers mentioned hereinabove include radiation-transmissive subbing and registration layers, which if used, are located between the reagent layer and the optional support layer. Subbing layers may also be included between other layers to provide the required adhesion and fluid contact between such layers. Such optional registration and subbing layers are known in the art and are described in U.S. Pat. No. 3,992,158, and in U.S. Pat. No. 4,042,335, both incorporated by reference hereinabove.

The detectable species migration-inhibiting layer of the present invention is interposed between the reagent layer and the porous radiation-blocking layer and is radiation-transmissive. The detectable species migration-inhibiting layer is permeable to the analyte, so that analyte can diffuse through it from the porous radiation-blocking layer and into the reagent layer. The detectable species migration-inhibiting layer functions such that a significant portion of any detectable species, e.g., a dye, migrating into it from the reagent layer is fixed in place or otherwise prevented from further migrating into the porous radiation-blocking layer (and further into the separate spreading layer, if one is present) wherein it cannot easily be measured. Detectable species migration-inhibiting layers of a preferred embodiment of the present invention comprise a hydrophilic colloid and a mordant for the particular detectable species formed in the reagent layer. Useful hydrophilic colloids include those mentioned hereinabove as useful in reagent layers of the described elements. Useful mordants are chosen according to the particular detectable species formed in the reagent layer. In the example of an element for the analysis of glucose in liquids, discussed above, one preferred mordant among others is a copolymer comprising recurring units of styrene; N-vinylbenzyl-N,N-dimethylbenzylammonium chloride; and divinyl benzene. It has been found that if the mordant is placed directly in the reagent layer, it often unexpectedly interferes with the reactions initiated by the presence of the analyte and prevents or significantly inhibits the formation or release of the detectable species.

Other mordants useful in the present invention include compounds of the structure:

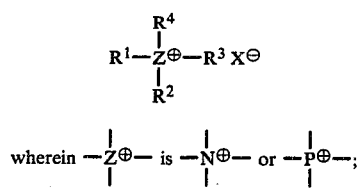

wherein $-Z^\oplus-$ is $-N^\oplus-$ or $-P^\oplus-$;

each of $R^1$, $R^2$ and $R^3$, which may be the same or different, is selected from alkyl, alkenyl, aralkyl, or aryl having less than about eight carbon atoms, including cycloalkyls such as cyclohexyl, alkenyls such as allyl, aralkyls such as benzyl, and aryls such as phenyl and substituted phenyls;

$R^4$ is a ballasting group having more than about 8 carbon atoms such as alkyl, including substituted alkyl and alkyl having hetero atoms or groups within or appended to the alkyl chain, aralkyl, and aryl as defined above; and $X^\ominus$ is an acid anion such as a halide ion, e.g., chloride or bromide; nitrate; methosulfate; p-toluenesulfonate; etc.

One example of a useful mordant of Formula I above is a compound having the structure:

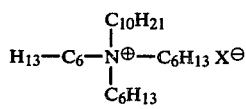

Other mordants useful in the invention are polymeric mordants including copolymers, e.g., terpolymers. A partial listing of representative useful polymeric mordants includes polymers having recurring units derived from 70 to about 98 weight percent of one or a mixture of hydrophobic monomers, for example, styrene; and recurring units derived from about 2 to 30, preferably about 5 to 20 weight percent, of cationic monomers, such units typically, but not necessarily, conforming to the structure:

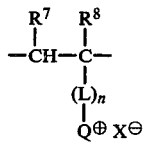

wherein
L is a chemical linking group between Q and the atoms in the chain of the polymer backbone;
n is 0 or 1;
$X^\ominus$ is an acid anion as defined above; and
$Q^\oplus$ is a linear or heterocyclic ammonium, phosphonium, or sulfur-containing group of the structure:

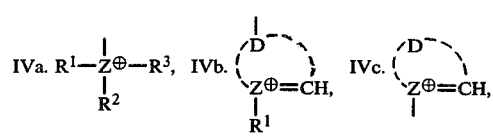

-continued

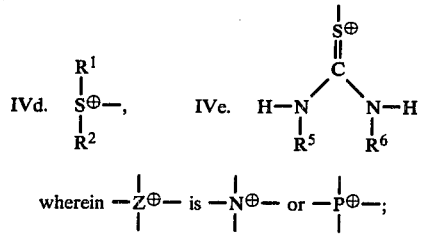

wherein $-Z^\oplus-$ is $-N^\oplus-$ or $-P^\oplus-$;

each of $R^1$, $R^2$, and $R^3$, which may be the same or different, is as defined above;
each of $R^5$, $R^6$, $R^7$, and $R^8$, which may be the same or different, represent H or $R^1$ as defined above; and
D is the atoms necessary to complete a heterocyclic ring. In addition to styrene other hydrophobic monomers useful as recurring units in these polymeric mordants include substituted styrenes, alkyl acrylates and methacrylates, difunctional monomers such as divinylbenzene and ethylenedimethacrylate, acrylamides, methacrylamides, and the like.

A partial listing of representative cationic monomers useful in preparing these polymeric mordants includes:
N-vinylbenzyl-N,N,N-trimethylammonium chloride,
N-benzyl-N,N-dimethyl-N-vinylbenzylammonium chloride,
N,N,N-trihexyl-N-vinylbenzylammonium chloride,
N-(3-maleimidopropyl)-N,N,N-trimethylammonium chloride,
N-benzyl-N-(3-maleimidopropyl)-N,N-dimethylammonium chloride,
N-vinyloxycarbonylmethyl-N,N,N-trimethylammonium chloride,
N-(3-acrylamido-3,3-dimethylpropyl)-N,N,N-trimethylammonium methosulfate,
1,2-dimethyl-5-vinylpyridinium methosulfate,
N-(2-hydroxy-3-methacryloyloxypropyl)-N,N,N-trimethylammonium chloride,
N-(2-hydroxy-3-methacryloyloxypropyl)-N,N,N-trimethylammonium sulfate,
N-(2-methacryloyloxyethyl)-N,N,N-trimethylammonium iodide,
N-(2-methacryloyloxyethyl)-N,N,N-trimethylammonium p-toluenesulfonate,
N-(2-methacryloyloxyethyl)-N,N,N-trimethylammonium methosulfate,
3-methyl-1-vinylimidazolium methosulfate,
N-(2-methacryloyloxyethyl)-N,N,N-trimethylammonium acetate,
N-(2-methacryloyloxyethyl)-N,N,N-trimethylammonium bromide,
N-(2-methacryloyloxyethyl)-N,N,N-trimethylammonium chloride,
N-(2-methacryloyloxyethyl)-N,N,N-trimethylammonium fluoride,
N-(2-methacryloyloxyethyl)-N,N,N-trimethylammonium nitrate, and
N-(2-methacryloyloxyethyl)-N,N,N-trimethylammonium phosphate.

An example of one suitable polymeric mordant of the type described is that copolymer identified hereinbefore as useful in an element for the analysis of glucose in liquids.

In addition to the use of mordants to formulate the detectable species migration-inhibiting layer used in the present invention, one can also employ as the migration-inhibiting material an antibody for the detectable species provided by the reagent layer. Such antibodies can be prepared by conventional immunological techniques and, of course, can vary widely depending on the particular material to be used as the detectable species in a given element of the invention. Typically, such antibodies are immobilized in the detectable species migration-inhibiting layer.

Exemplary elements of this invention includes those illustrated in the accompanying drawings. In FIG. 1 is represented an analytical element composed of a reagent layer 12, a detectable species migration-inhibiting layer 14, a porous radiation-blocking layer 16, and, optionally, a spreading layer 18. All of these layers are in substantially continuous intimate contact with their adjacent layers. In an alternative embodiment of the invention, shown in FIG. 2, the analytical element is composed of a support 20 on which is coated a reagent layer 24, a detectable species migration-inhibiting layer 26, and a porous radiation-blocking layer 28, which in this case serves also as a spreading layer. Optionally, either or both subbing and registration layers 22 may also be included in the analytical element. All of these layers are in substantially continuous intimate contact with their adjacent layers.

Figure 2:
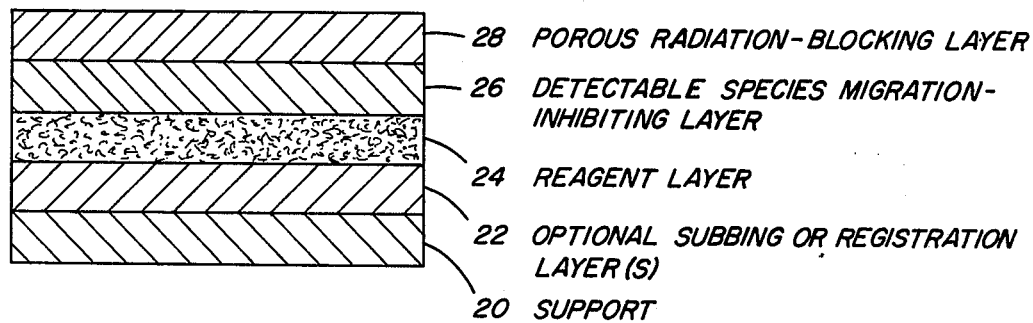
FIG. 2 is an enlarged sectional view illustrating a preferred embodiment of an analytical element of this invention.

In the practice of this invention, a sample of a liquid to be analyzed is placed on the outermost surface layer of the element, which in the case of the element illustrated in FIG. 2 is the porous, radiation-blocking, spreading layer 28. Any predetermined analyte present in this liquid diffuses through the porous, radiation-blocking layer and the detectable species migration-inhibiting layer, and enters the reagent layer. There, interaction with the test reagents causes the release of or the formation of a detectable species such as a dye. This dye either remains in place or in part migrates out of the reagent layer, into the detectable species migration inhibiting layer, and also into any porous, radiation-transmissive layers underlying the reagent layer. All or most of the dye entering the detectable species migration-inhibiting layer is fixed in place and prevented from further migrating into the overlying porous radiation-blocking layer or layers. The reflective density of all dye in the detectable species migration-inhibiting layer, the reagent layer, and any other underlying radiation-transmissive layers is then determined while the element is still intact by measuring this density spectrophotometrically through all of these radiation-transmissive layers at the same time.

The following examples are provided to further illustrate certain embodiments of the present invention.

EXAMPLE 1

Element For the Analysis Of Glucose

Two elements for the analysis of glucose in liquids were prepared in the following manner:

Polyethylene terephthalate film supports were coated with reagent layers comprising peroxidase at 10,200 U/m$^2$, (the symbol U refers to international units, which are the well known and generally accepted units of measurement of enzyme activity), glucose oxidase at 24,400 U/m$^2$, 7-hydroxy-1-naphthol at 0.66 g/m$^2$, and 4-aminoantipyrene hydrochloride at 0.86 g/m$^2$. The reagent layer of control sample 1 further comprised deionized gelatin at 21.5 g/m$^2$. The reagent layer of sample 2 also comprised deionized gelatin, but at 19.4 g/m$^2$. The second sample was then coated with a detectable species migration-inhibiting layer, in this case a dye migration-inhibiting layer comprising deionized gelatin at 2.1 g/m$^2$ and the mordant, poly(styrene-co-N-vinylbenzyl-N,N-dimethylbenzylammonium chloride-co-divinyl benzene) (weight ratio 49.5:49.5:1.0) at 1.08 g/m$^2$. All gelatin-containing layers were buffered at pH 6.0 with a disodium phosphate-potassium phosphate buffer. Both samples were then overcoated with a subbing layer comprising n-isopropylacrylamide at 0.32 g/m$^2$ and a blushed-polymer, radiation-blocking, spreading layer comprising cellulose acetate at 9.4 g/m$^2$ and titanium dioxide at 64.5 g/m$^2$.

The two resulting elements were then contacted at the outermost surface of their spreading layers with 10 μl samples of glucose standards containing various concentrations of glucose. After 7 minutes of contact at 37° C. the reflection densities of the dye formed were measured spectrophotometrically using a photomultiplier unit and a Wratten 65 filter. The following Table I illustrates the results, the control sample being representative of elements of the prior art.

TABLE I

| Effect of Dye Migration-Inhibiting Layer on Measurement of Density of Dye Formed in Element For Glucose Assay | | |
|---|---|---|
| Actual Glucose Concentration (mg/dl) | Measured Dye Density in Control Sample ($D_R$) | Measured Dye Density in Sample Containing Dye Migration-Inhibiting Layer ($D_R$) |
| 100 | 0.44 | 0.60 |
| 200 | 0.80 | 1.00 |
| 400 | 1.23 | 1.65 |
| 800 | 1.84 | 2.03 |

EXAMPLE 2

Element For The Analysis Of Calcium

Two elements, one with and the other without a detectable species migration-inhibiting layer containing a mordant, were prepared according to the following:

A terephthalate film support was coated with a reagent layer comprising gelatin (4.3 g/m$^2$), Triton X-100 (0.17 g/m$^2$), chorophosphonazo III (0.21 g/m$^2$), bis(-vinylsulfonylmethyl) ether (0.04 g/m$^2$) and 0.1 M 3,3-dimethylglutaric acid, pH 5.4; a dye migration-inhibiting layer comprising gelatin (4.3 g/m$^2$), and poly(styrene-co-N-vinylbenzyl-N,N-dimethylbenzyl ammonium chloride-co-divinylbenzene) (2.15 g/m$^2$); a subbing layer comprising (poly-N-isopropylacrylamide) (0.32 g/m$^2$); and a blushed-polymer, radiation-blocking spreading layer comprising TiO$_2$ (50.4 g/m$^2$), cellulose acetate (7.0 g/m$^2$) and Triton X-405 (1.4 g/m$^2$).

A second control element (outside the scope of the present invention) was prepared in the same manner except without a detectable species migration-inhibiting layer between the spreading layer and reagent layer.

The elements were evaluated as in Example 1, using calcium standards containing 1 to 5 mM of calcium and reading the reflection densities at 670 nm. Table II shows the improved results obtained with the element containing the detectable species migration-inhibiting layer, in this case a dye migration-inhibiting layer.

The results of Examples 1 and 2 above indicate that a significantly higher dye density was consistently measured with the element containing a detectable species migration-inhibiting layer. The control element, having no such layer, allowed significant amounts of the dye to migrate into the blushed-polymer, radiation-blocking, spreading layer where it could not be detected.

TABLE II

Effect of Dye Migration-Inhibiting Layer on Measurement of Density of Dye Formed in Element For Calcium Assay

| Actual Calcium Concentration (mM) | Measured Dye Density in Control Sample ($D_R$) | Measured Dye Density in Sample Containing Dye Migration-Inhibiting Layer ($D_R$) |
|---|---|---|
| 0 | 0.246 | 0.28 |
| 1 | 0.267 | 0.75 |
| 2 | 0.269 | 0.80 |
| 3 | 0.279 | 0.82 |
| 4 | 0.269 | 0.84 |
| 5 | 0.262 | 0.84 |

EXAMPLE 3

Example No. 2 was repeated, except that the reagent layer contained as a calcium indicator 0.48 g/m² arsenazo III, rather than chlorophosphonazo III. The reagent layer was buffered to a pH of 5.6. The resulting element demonstrated a dye density comparable to that of the test element of Example 2.

The invention has been described in detail with particular reference to certain preferred embodiments thereof, but it will be understood that variations and modifications can be effected within the spirit and scope of the invention.

We claim:

1. In an element for the analysis of liquids, said element comprising a radiation-transmissive reagent layer permeable to a predetermined analyte, which layer comprises a composition that is interactive in the presence of said analyte to provide a radiometrically detectable species, and a porous radiation-blocking layer permeable to said analyte;

the improvement comprising a radiation-transmissive, detectable species migration-inhibiting layer interposed between the reagent layer and the porous radiation-blocking layer, said detectable species migration-inhibiting layer being permeable to said analyte and inhibiting the migration of said radiometrically detectable species to said porous radiation-blocking layer upon contact of said element with the liquid under analysis.

2. An element as described in claim 1 wherein said detectable species migration-inhibiting layer comprises an immobilized antibody for said radiometrically detectable species.

3. In an element for the analysis of liquids, said element comprising a radiation-transmissive reagent layer permeable to a predetermined analyte, which layer comprises a composition that is interactive in the presence of said analyte to provide a dye, and a porous radiation-blocking layer permeable to said analyte;

the improvement comprising a radiation-transmissive, dye migration-inhibiting layer interposed between the reagent layer and the porous radiation-blocking layer, said dye migration-inhibiting layer being permeable to said analyte and inhibiting the migration of said dye to said porous radiation-blocking layer upon contact of said element with the liquid under analysis.

4. In an element for the analysis of liquids, said element comprising a radiation-transmissive reagent layer permeable to a predetermined analyte, which layer comprises a composition that is interactive in the presence of said analyte to provide a radiometrically detectable species, a spreading layer permeable to said analyte, and a porous radiation-blocking layer, permeable to said analyte and interposed between said reagent layer and said spreading layer;

the improvement comprising a radiation-transmissive, detectable species migration-inhibiting layer interposed between the reagent layer and the porous radiation-blocking layer, said detectable species migration-inhibiting layer being permeable to said analyte and inhibiting the migration of said radiometrically detectable species to said porous radiation-blocking layer upon contact of said element with the liquid under analysis.

5. In an element for the analysis of liquids, said element comprising a radiation-transmissive support having thereon a radiation-transmissive reagent layer permeable to a predetermined analyte, which layer comprises a composition that is interactive in the presence of said analyte to provide a dye, and an outermost radiation-blocking spreading layer permeable to said analyte;

the improvement comprising a radiation-transmissive, dye migration-inhibiting layer interposed between the reagent layer and the radiation-blocking spreading layer, said dye migration-inhibiting layer being permeable to said analyte and inhibiting the migration of said dye to said radiation-blocking spreading layer upon contact of said element with the liquid under analysis.

6. An element as described in claim 5 which further comprises at least one radiation-transmissive registration layer interposed between said reagent layer and said support.

7. An element as described in claim 5 which further comprises a radiation-transmissive subbing layer interposed between said reagent layer and said support.

8. An element as described in claim 5 wherein the dye migration-inhibiting layer comprises a mordant for said dye.

9. An element as described in claim 5 wherein the dye migration-inhibiting layer comprises a mordant for the dye, said mordant having the structure $$R^1-\underset{R^2}{\overset{R^4}{\underset{|}{\overset{|}{Z^\oplus}}}}-R^3 \; X^\ominus$$

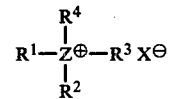

each of $R^1$, $R^2$ and $R^3$, which may be the same or different, is selected from alkyl, alkenyl, aralkyl, or aryl having less than about eight carbon atoms;

$R^4$ is a ballasting group having more than about 8 carbon atoms; and $X^\ominus$ is an acid anion.

10. An element as described in claim 5 wherein the dye migration-inhibiting layer comprises a mordant for the dye, said mordant being polymeric and containing a recurring unit having the structure

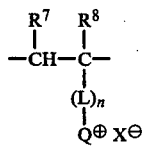

wherein
L is a linking group between Q and the atoms in the chain of the polymer backbone;
n is 0 or 1;
$X^\ominus$ is an acid anion; and
$Q^\oplus$ is a linear or heterocyclic ammonium, phosphonium, or sulfur-containing group having one of the following structures:

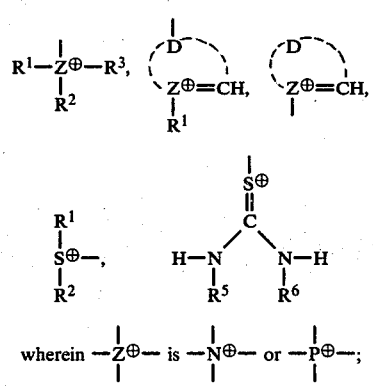

each of $R^1$, $R^2$, and $R^3$, which may be the same or different, is selected from alkyl, alkenyl, aralkyl, or aryl having less than about 8 carbon atoms;
each of $R^5$, $R^6$, $R^7$, and $R^8$, which may be the same or different, represent H or $R^1$ as defined above; and
D is the atoms necessary to complete a heterocyclic ring.

11. An element as described in claim 5 wherein the dye migration-inhibiting layer comprises a hydrophilic colloid.

12. In an element for the analysis of liquids, said element comprising a radiation-transmissive support having thereon a radiation-transmissive reagent layer permeable to a predetermined analyte, which layer comprises a composition that is interactive in the presence of said analyte to provide a dye, and an outermost radiation-blocking spreading layer permeable to said analyte;

the improvement comprising a radiation-transmissive, dye migration-inhibiting layer interposed between the reagent layer and the radiation-blocking spreading layer, said dye migration-inhibiting layer being permeable to said analyte and comprising a hydrophilic colloid and a mordant for said dye.

13. An element as described in claim 12 wherein the radiation-blocking spreading layer comprises a blushed polymer and a pigment.

14. An element as described in claim 12 wherein the reagent layer comprises a hydrophilic colloid having said interactive composition distributed therein.

15. In an element for the analysis of liquids, said element comprising a radiation-transmissive support having thereon a radiation-transmissive reagent layer permeable to a predetermined analyte, which layer comprises a hydrophilic colloid, said colloid having distributed therein a composition that is interactive in the presence of said analyte to provide a dye; and an outermost radiation-blocking spreading layer, permeable to said analyte, comprising a finely-divided particulate pigment and a blushed polymer;

the improvement comprising a radiation-transmissive dye migration-inhibiting layer, interposed between the reagent layer and the radiation-blocking spreading layer, said dye migration-inhibiting layer being permeable to said analyte and comprising a mordant for said dye and a hydrophilic colloid.

16. An element as described in claim 15 wherein the reagent layer is permeable to glucose and wherein the interactive composition in the reagent layer comprises glucose oxidase, peroxidase, and an indicator composition comprising a compound oxidizable in the presence of hydrogen peroxide and peroxidase to effect formation of said dye.

17. An element as described in claim 15 wherein the reagent layer is permeable to calcium and wherein the interactive composition in the reagent layer comprises an indicator for calcium.

* * * * *